(12) United States Patent  
Phin (10) Patent No.: US 10,429,324 B2  
(45) Date of Patent: Oct. 1, 2019

(54) RADIOGRAPHIC PIPE INSPECTION METHOD AND APPARATUS

(71) Applicant: PARAGON INSPECTION LIMITED, Dundee Tayside (GB)

(72) Inventor: David Sutherland Phin, Dundee Tayside (GB)

(73) Assignee: Paragon Inspection Limited, Dundee Tayside (GB)

(*) Notice: Subject to any disclaimer, the term of this patent is extended or adjusted under 35 U.S.C. 154(b) by 99 days.

(21) Appl. No.: 15/033,164

(22) PCT Filed: Oct. 29, 2014

(86) PCT No.: PCT/GB2014/053220  
§ 371 (c)(1),  
(2) Date: Apr. 29, 2016

(87) PCT Pub. No.: WO2015/063483  
PCT Pub. Date: May 7, 2015

(65) Prior Publication Data  
US 2016/0266055 A1    Sep. 15, 2016

(30) Foreign Application Priority Data  
Nov. 1, 2013 (GB) .................................. 1319319.8

(51) Int. Cl.  
*G01N 23/18* (2018.01)

(52) U.S. Cl.  
CPC ....... *G01N 23/18* (2013.01); *G01N 2223/301* (2013.01); *G01N 2223/628* (2013.01)

(58) Field of Classification Search  
CPC ............. G01N 23/18; G01N 2223/301; G01N 2223/628; A61B 6/44  
See application file for complete search history.

(56) References Cited

U.S. PATENT DOCUMENTS 3,666,944 A * 5/1972 Baldinger ............... G01N 23/04  
250/496.1  
3,686,932 A * 8/1972 Ries ....................... G01N 23/18  
378/59  
(Continued)

FOREIGN PATENT DOCUMENTS

AU          662313         8/1995  
GB         2157930        10/1985  
(Continued)

OTHER PUBLICATIONS

Search Report conducted in related application GB 1319319.8, dated Jan. 29, 2014.

(Continued)

*Primary Examiner* — Dani Fox  
*Assistant Examiner* — Soorena Kefayati  
(74) *Attorney, Agent, or Firm* — Meunier Carlin & Curfman LLC (57) ABSTRACT

A method of inspecting a pipe includes locating a container around a pipe when the container is in an open position and moving the container from the open to a closed position. Then passing radiation through the container and at least a portion of the pipe substantially enclosed by the container. The distance between a source of the radiation and the at least a portion of the pipe being equal to or less than 300 mm. An apparatus comprising a container moveable between an open and a closed position. In the open position the container is locatable around a pipe and in the closed position the container substantially encloses at least a portion of the pipe. In the closed position the distance between a source of radiation enclosed in the container and the at least a portion of the pipe is equal to or less than 300 mm.

23 Claims, 4 Drawing Sheets

(56) References Cited

U.S. PATENT DOCUMENTS

| | | | |
|---|---|---|---|
| 3,737,661 A | 6/1973 | Applegate | |
| 3,835,323 A * | 9/1974 | Kahil | G01N 23/18 250/366 |
| 3,944,831 A * | 3/1976 | Heisner | G01M 17/028 378/61 |
| 4,187,425 A * | 2/1980 | Thompson | G01N 23/18 378/59 |
| 4,543,482 A * | 9/1985 | Brenholdt | G01N 21/53 250/343 |
| 4,866,745 A * | 9/1989 | Akai | A61B 6/032 378/9 |
| 4,974,246 A * | 11/1990 | Heiskel | G01N 23/04 378/54 |
| 5,042,055 A * | 8/1991 | Wirt | G01B 15/045 378/56 |
| 5,388,129 A * | 2/1995 | Hartley | G21C 17/00 376/249 |
| 5,420,427 A * | 5/1995 | Morgan | G01N 23/18 250/358.1 |
| 5,614,720 A * | 3/1997 | Morgan | G01N 23/18 250/358.1 |
| 5,698,854 A * | 12/1997 | Gupta | G01N 23/18 250/358.1 |
| 5,963,030 A * | 10/1999 | Stark | G01B 7/12 324/228 |
| 5,978,440 A * | 11/1999 | Kang | G01N 23/046 378/21 |
| 6,226,353 B1 * | 5/2001 | Wilkins | A61B 6/484 378/98.11 |
| 6,466,643 B1 * | 10/2002 | Bueno | G01N 23/04 378/58 |
| 7,284,433 B2 | 10/2007 | Ales et al. | |
| 7,412,026 B2 * | 8/2008 | Liu | A61B 6/484 378/62 |
| 7,656,997 B1 * | 2/2010 | Anjelly | G01N 23/04 378/59 |
| 7,885,381 B2 * | 2/2011 | Nagumo | G01B 15/025 378/41 |
| 8,759,780 B2 * | 6/2014 | Dobbs | G01B 15/02 250/360.1 |
| 8,923,478 B2 * | 12/2014 | Knight | G01N 23/18 250/257 |
| 9,217,720 B2 * | 12/2015 | Prentice | B23K 31/125 |
| 9,389,150 B2 * | 7/2016 | Kimpel, Jr. | G01M 99/00 |
| 9,726,569 B2 * | 8/2017 | Koyanagi | G01N 23/025 |
| 2005/0041775 A1 * | 2/2005 | Batzinger | G01N 23/04 378/59 |
| 2008/0267345 A1 * | 10/2008 | Nagumo | G01B 15/025 378/11 |
| 2010/0174184 A1 * | 7/2010 | Kimchy | A61B 6/4057 600/436 |
| 2011/0122990 A1 * | 5/2011 | Dafni | A61B 6/032 378/4 |
| 2011/0168900 A1 * | 7/2011 | Dobbs | G01B 15/02 250/360.1 |
| 2012/0140876 A1 * | 6/2012 | Jung | G01N 23/046 378/20 |
| 2012/0201347 A1 * | 8/2012 | Prentice | B23K 31/125 378/59 |
| 2013/0148787 A1 * | 6/2013 | Campbell | G01T 1/2018 378/62 |
| 2013/0193338 A1 * | 8/2013 | Wuestenbecker | G01N 23/083 250/393 |
| 2015/0373822 A1 * | 12/2015 | Churchman | G01N 23/04 378/59 |

FOREIGN PATENT DOCUMENTS

| | | | | |
|---|---|---|---|---|
| GB | 2157930 A | * | 10/1985 | G01N 23/18 |
| GB | 2157930 A | * | 10/1985 | G01N 23/18 |
| JP | 09133283 | | 5/1997 | |
| WO | 2005024406 | | 3/2005 | |
| WO | 2008083993 | | 7/2008 | |
| WO | 2010033265 | | 3/2010 | |
| WO | 2011023960 | | 3/2011 | |

OTHER PUBLICATIONS

International Search Report for International Patent Application No. PCT/GB2014/053220, dated Feb. 3, 2015, 4 pages.
Examination Report for International Patent Application No. EP14793251.1, dated Dec. 22, 2017, 6 pages.

* cited by examiner

RADIOGRAPHIC PIPE INSPECTION METHOD AND APPARATUS

The present invention relates to an apparatus and method for inspecting the integrity of pipes and pipe fittings.

Two sections of pipe or a pipe and valve, meter, flow control device and so on are commonly connected together using a union. Other fittings such as T-pieces and elbows are used to adapt the shape of the pipe and subsequent pipework or fluid circuit and the flow path through the pipe or fluid circuit to match the given requirements.

The integrity of any connection between two sections of pipe or a section of pipe and a pipe union or fitting depends on the correct fitment of the union or fitting to the section of pipe. Once the union or fitting is attached to the pipe and the resulting assembly completed it is however difficult to assess whether the connection has been made properly.

A pipe end could be partially or incompletely fitted within a body of the fitting by virtue of the assembler failing to properly insert the pipe end sufficiently into the body of the fitting in accordance with the manufacturer's instructions. Vibration effects, temperature variations and other atmospheric conditions may also cause the pipe end to become loose and/or a gap to appear between the pipe end and the fitting abutment face or the pipe to become detached from the fitting.

Pipe unions or fittings are secured to an end of a section of pipe using a wide variety of designs including but not limited to single ferrule and multi ferrule fittings, various clamping arrangements using elastomeric seals, gripping rings, nuts and so on.

Abutment of the end of the pipe with a mating face of the body of the fitting or other type of connection face is usually desirable as it allows a gripping device such as a ferrule to be installed onto the pipe without the pipe moving axially. A nut is normally used to compress the ferrule onto the pipe and thereby secure the ferrule to the pipe, ensuring a proper fluid tight seal and strong grip on the pipe end ensuring a strong mechanical assembly such that the assembly can withstand environmental conditions such as vibration effects and temperature variations.

The pipe and ferrule are located in the fitting or union and the nut used to hold the ferrule and therefore also the pipe in the fitting or union. The position of the ferrule on the pipe determines the position of the end of the pipe in the union or fitting. Proper connection between the pipe and the union or fitting may depend on the pipe being secured in the fitting or union without a gap between an end face of the pipe and an internal mating surface of the union or fitting. Proper connection may also depend on the square alignment of the end of the pipe within the body of the fitting and/or the general quality of the bottoming of the pipe end within the fitting.

A gap will commonly result in a reduction of the pressure rating of the fitting or fluid leaking from the pipe. Incorrect ferrule fitment and improper nut tightening and thread engagement can also result in a reduction of the pressure rating and fluid leaks.

The inventor of the present invention has developed an apparatus for and method of assessing the integrity of a mechanical connection between a pipe and mating or abutment surface of another fluid flow coupling or element such as a pipe fitting, such that a gap between the pipe and a mating or abutment surface within a fluid flow coupling installed on the pipe can be detected and/or assessed, without the need to remove the pipe fitting from the pipe.

In accordance with a first aspect of the present invention there is provided an apparatus comprising:
- a container comprising a first portion and a second portion, the container being moveable between an open and a closed position, wherein in the open position the container is locatable around a pipe and in the closed position the container substantially encloses at least a portion of the pipe; and
- a source of radiation enclosed in the container;
- wherein in the closed position the distance between the source of radiation and the at least a portion of the pipe is equal to or less than 300 mm.

It is an advantage of the present invention that the container encloses the source of radiation and at least substantially encloses the at least a portion of the pipe. This helps to protect the surrounding environment, including nearby objects and personnel, from the radiation source. This is possible when the distance between the source of radiation and the at least a portion of the pipe is equal to or less than 300 mm.

The source of radiation may be one or more of electromagnetic, ionising and particulate radiation. In use, the source of radiation may produce a beam or stream of electromagnetic, ionising or particulate radiation.

It is also an advantage of the present invention that the container can be locatable around the pipe when the pipe is in situ and/or in position.

The distance between the source of radiation and the portion of the pipe or pipe fitting may be equal to or less than 100 mm and may be equal to or less than 10 mm. The distance may depend on the diameter of the pipe or pipe fitting to be examined within the container and/or the source of radiation used.

The pipe may have a pipe fitting at one end. In the closed position the container typically substantially encloses the at least a portion of the pipe and the pipe fitting. The pipe fitting may be referred to as a mechanical connection and may be one or more of a union, a coupling, an elbow, a T-piece, a cap, and a valve or any other type of pipe connection coupling or various clamping arrangements using elastomeric seals gripping rings, nuts and so on.

The first and second portions of the container may be connectable such that when the first and second portions are connected they form the container and typically a chamber of the container. The container may comprise any number of portions.

One side of the first and second portions of the container may be connected by a hinge. Another side of the first and second portions of the container may be connected by a pin or clasp or other means of engagement. The first and second portions of the container may be rotatable relative to one another, thereby moving the container between the open and closed positions. The second portion may be referred to as a shutter.

In an alternative embodiment the first and second portions may be separable. When the first and second portions are separable, the first portion of the container may be locatable over a portion of the pipe and the second portion of the container locatable over the same portion of the pipe, thereby enclosing the portion of the pipe.

The first portion of the container may contain the source of radiation.

The container of the apparatus may be a first container and the apparatus may further comprise a second container. The second container may be attachable to the first container. The second container may contain the source of radiation.

The first container may have an aperture for communication with an aperture in the second container. The apertures may be aligned such that the source of radiation in the second container can provide the source radiation in the first container.

The apparatus may further comprise a safety system to stop or at least mitigate the emission of radiation from the source into the container, when the container is in the open position. The safety system may be a shield locatable between the source of the radiation and the chamber of the container. In one embodiment the shield may be locatable between the first and second containers and may be locatable so as to block the apertures in the first and second containers. In another embodiment the second portion of the container may also be the shield.

In another embodiment the safety system may disable the source of radiation such that it is contained and/or cannot be accessed without a key when the container is in the open position.

The source of radiation may be exposed to the at least a portion of the pipe when the container is in the closed position.

The pipe may have an outer diameter of from 5 to 500 mm, typically from 5 to 100 mm and normally from 5 to 50 mm. The pipe may be referred to as a tube or tubing and/or small-bore tubing. The pipe may be suitable for the transportation of fluid or solid material. Whether the material is a gas, a liquid or a solid will typically depending on temperature and/or pressure of the material. The material may form part of a multiphase transport system. The fluid may be a hydrocarbon, for example natural gas or crude oil. The pipe may be made of metal or another material, including plastic.

In use, the pipe typically passes through the centre of the container.

In use, the source of radiation may emit radiation and typically emits a beam of radiation. The radiation is typically ionising radiation and preferably x-ray or gamma radiation or particulate radiation. The source of radiation typically has a wavelength of equal to or less than 100 nanometers. The source of radiation typically transfers energy in the form of particles or electromagnetic waves. The source of radiation typically has a frequency of equal to or more than $3 \times 10^{15}$ Hz. The source of radiation is typically capable of directly or indirectly producing ions. It will be appreciated by those skilled in the art that the invention may be used with any conveniently available form of electromagnetic, ionising or particulate energy.

The radiation may be one or more of Ytterbium 169, Thulium 170, Selenium 75, alpha or beta particles and neutrons. The source of radiation may be in the form of a capsule.

The energy of the radiation may be chosen to suit the particular application. The container is normally a relatively small, portable, handheld device that can provide limited or total shielding of the source of radiation.

The apparatus may be portable, that is the apparatus is typically hand held and/or moveable between many different pipes and pipe fittings.

The radiation may be particularly adapted to the radiography of thin metals or non-metallic materials. High and medium pressure pipe and pipe fittings are typically made of metal. The radiation may be particularly suited to measuring and/or determining the thickness of metal from 20 to 0.25 mm, typically from 15 to 0.25 mm and normally from 10 to 0.25 mm.

The source of radiation may be periodically replaced with a new source of radiation.

The apparatus may be referred to as an inspection apparatus. The apparatus may be used to inspect pipes and more particularly to inspect the integrity of a joint between two sections of pipe or between a section of pipe and a fitting at one end of the pipe. The apparatus may be used to determine if there is a gap between the pipe and the pipe fitting. The apparatus may be used to assess the integrity of a pipe fitting without disassembling the pipe fitting from the pipe. The apparatus may be used to determine the relative or axial position of an end of the pipe when the end of the pipe is inside the pipe fitting.

The apparatus may be also be used to assess the integrity of a pipe and in particular the thickness of a wall of the pipe. Corrosion or erosion of the pipe may reduce the thickness of the wall of the pipe.

The apparatus may also be used to determine pipe or fitting blockages cracks or other discontinuities.

The container typically houses a radiation detector. The detector is typically used to determine the strength, quantity and/or amount of radiation. The strength of radiation can be chosen so that no radiation reaches the detector if the pipe and pipe fitting are properly connected. In use, the radiation may penetrate through the pipe and/or pipe fitting and/or ferrule/s before being detected by the detector.

The strength, quantity and/or amount of radiation passable through the container may be compared to the strength, quantity and/or amount of radiation passable through the pipe and/or pipe fitting. A gap between the pipe and the pipe fitting or a portion of the pipe where the thickness of the wall has been reduced will result in an increase in the radiation impinging on and/or being detected by the detector.

Also, a blockage in a pipe or pipe fitting will result in a decrease in the radiation impinging on and/or being detected by the detector. The strength of the radiation may be such that little or no radiation reaches the detector when there is a blockage in the pipe.

The pipe fitting may be secured to an end of a section of pipe using a nut and ferrule/s. The nut is normally used to compress the ferrule onto the pipe and thereby secure the ferrule to the pipe. The pipe and ferrule are located in the fitting and the nut used to hold the ferrule and therefore also the pipe in the fitting. The position of the ferrule on the pipe determines the position of the end of the pipe in the union or fitting. Proper connection, sealing and pressure ratings between the pipe and the pipe fitting depends on the pipe being secured to the fitting without a gap between the end or an end face of the pipe and an internal mating surface of the fitting.

Incorrect fitment of the ferrule at the end of the pipe, a reversed back ferrule in a two ferrule system and/or the incorrect thread engagement of the nut with the pipe fitting can also be assessed using the apparatus according to the first aspect of the present invention.

The detector may be any type of radiation detector for example a film, Geiger-Mueller (GM) tube, ion chamber, scintillation counter or screen, proportional counter, spark chamber, semiconductor, solid state, flat panel, digital panel, phosphor or imaging plates, amorphous silicon, screen or Charge-Coupled Device (CCD) detector.

The detector may be calibrated using a pipe having a known wall thickness and/or pipe and pipe fittings that have been correctly or incorrectly connected together and/or a pipe with a blockage. The detector may be connected to a display, output device or other electronic device or may be read by another device to generate an image, audible or visual output.

The distance between the source of radiation and the at least a portion of the pipe may be maintained, that is the distance may be the same throughout the time the at least a portion of the pipe is exposed to the radiation and may be the same for different portions of the pipe and pipe fittings having the same outer diameter. The distance will typically vary when the portions of pipe and pipe fittings have different external diameters.

The apparatus may further comprise a collimator. The beam of radiation typically passes through the collimator. The width of the beam that exits the collimator is typically narrower than the beam of radiation that enters the collimator. The collimator may reduce the scatter of the radiation from the source of radiation.

The apparatus of the present invention may be a non-destructive test to determine the mechanical connection and/or abutment condition of a pipe within a pipe fitting even when there is fluid or solid in the pipe. There may therefore be no need to purge the pipe or system comprising the pipe or disassemble any components of the system to undertake the test.

In accordance with a second aspect of the present invention there is provided a method of inspecting a pipe, the method including the steps of:
  providing a container comprising a first portion and a second portion;
  locating the container around a pipe when the container is in an open position;
  moving the container from the open position to a closed position, wherein in the closed position the container is located around the pipe and substantially encloses at least a portion of the pipe; and
  passing radiation through the container and the at least a portion of the pipe, the distance between a source of the radiation and the at least a portion of the pipe being equal to or less than 300 mm.

It is an advantage of the present invention that the method includes the step of enclosing a least a portion of the pipe in the container. This helps to protect the surrounding environment, including nearby objects and personnel, from the radiation when the container is in the closed position.

The step of passing radiation through the container may be referred to as radiation crossing the container. The step of passing radiation through the container may include passing radiation through the at least a portion of the pipe. The at least a portion of the pipe may include a pipe fitting.

The source of radiation may be enclosed in the container or be provided by a detachable radiation source.

The method may include the step of comparing the strength or quantity of the radiation able to pass through the pipe and/or pipe fitting with the strength of the radiation able to pass through the container or through an incorrectly fitted pipe and pipe fitting.

The radiation may be detected and/or measured using a detector. When there is a gap between the pipe and the pipe fitting or a portion of pipe where the thickness of the wall of the pipe has been reduced, the amount of radiation that is able to pass through the pipe and pipe fitting or wall of the pipe and therefore the amount of radiation impinging on and/or being detected by the detector will be increased, compared to a correctly connected pipe and pipe fitting where there is no gap or pipe where the thickness of the wall has not been reduced.

The container may further comprise a slot. The detector may fit through the slot such that the detector can be inserted into and removed from the container. The detector may be inserted through the slot, an image of the pipe or fitting features captured and then the detector removed from the slot after exposure of the pipe or pipe fitting. The detector may also be attached to the container such that a visual, audible or any other means of detection may be used. The detector may be connected to an electronic device or an output to notify the user audibly or visually of the condition of for example the connection between the pipe and pipe fitting.

The optional features of the first aspect of the present invention can be incorporated into the second aspect of the present invention and vice versa.

Embodiments of the present invention will now be described by way of example only and with reference to the accompanying drawings, in which.

Figure 1:
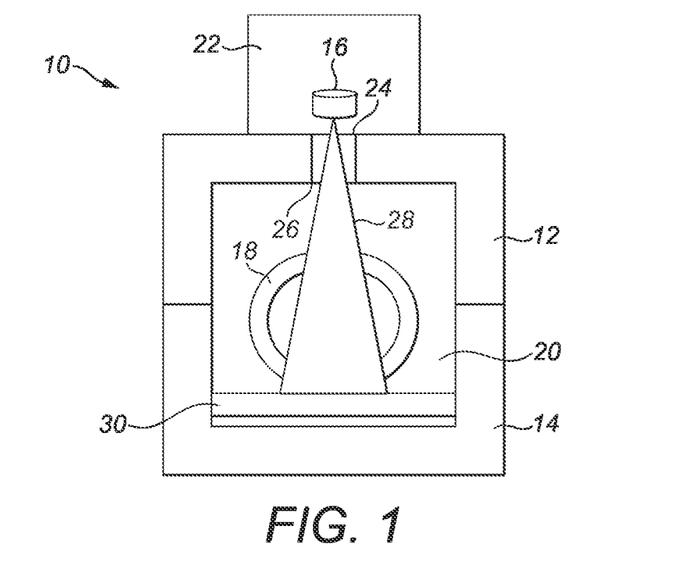
FIG. 1 is a cross-sectional view of a first embodiment of the apparatus according to the present invention.

FIG. 1 shows a cross-sectional view of the apparatus 10 according to the present invention. The apparatus 10 includes a container comprising first 12 and second 14 portions. The container 12, 14 is moveable between an open and a closed position.

The source of radiation 16 is enclosed in the container 12, 14. In the open position the container 12, 14 is locatable around a pipe 18 and in a closed position the container 12, 14 substantially encloses at least a portion of the pipe 18.

The pipe 18 has a pipe fitting (not shown) at one end. In the closed position the container, as shown in FIG. 1, substantially encloses the least a portion of the pipe 18 and the pipe fitting (not shown).

The first 12 and second 14 portions of the container are connectable such that when the first and second portions are connected they form the container and a chamber 20 of the container. The first 12 and second 14 portions are separable.

The apparatus 10 also includes a second container 22 or x-ray generator (not shown). The second container 22 or x-ray generator (not shown) is attached to the first portion 12 of the container. The source of radiation 16 is housed in the second container 22 or x-ray generator (not shown).

The first portion of the container 12 has an aperture 26 for communication with an aperture 24 in the second container 22 or x-ray generator (not shown). The apertures 24, 26 are aligned such that the source of radiation 16 in the second container 22 or x-ray generator (not shown) provides the radiation in the container 12, 14 and therefore also the chamber 20.

In use, the source of radiation 16 emits a beam of radiation 28.

The container 12, 14 houses a radiation detector 30. The detector 30 is used to determine the strength or amount of radiation.

Figure 2:
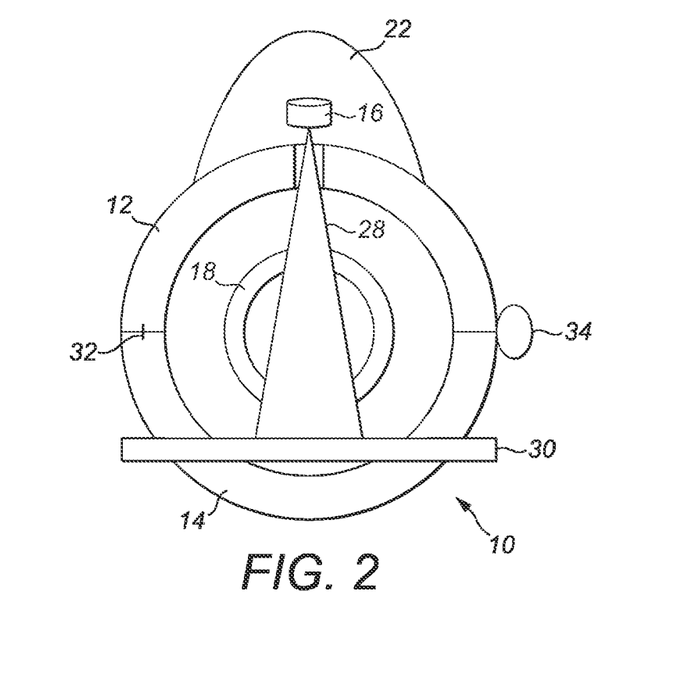
FIG. 2 is a cross-sectional view of a second embodiment of the apparatus.

FIG. 2 shows a cross-sectional view of a second embodiment of apparatus 10, also referred to as a two piece container. One side of the first 12 and second 14 portions of the container are connected by a hinge 32. The other side of the first 12 and second 14 portions of the container are connected by a pin 34. Other features of the apparatus 10 shown in FIG. 2 that are also shown in FIG. 1 have been labelled with the same reference numbers.

Figure 3:
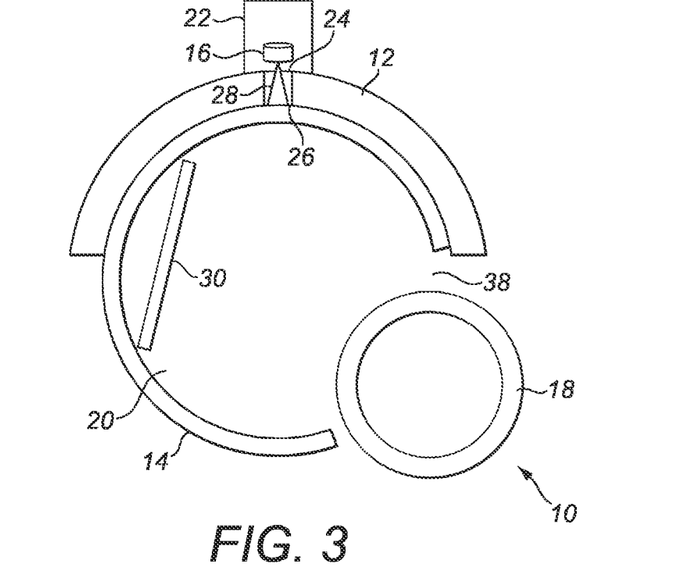
FIG. 3 is a cross-sectional view of a third embodiment of the apparatus in an open configuration.
Figure 4:
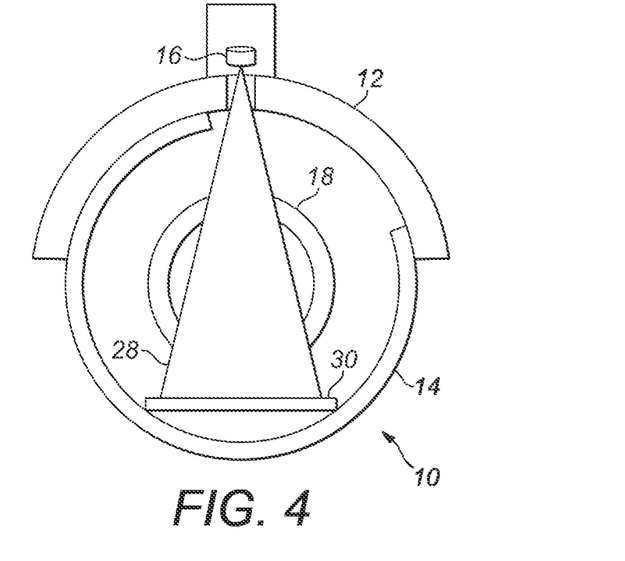
FIG. 4 is a cross-sectional view of the third embodiment of the apparatus in a closed configuration.

FIGS. 3 and 4 show cross-sectional views of a third embodiment of the apparatus 10 in an open and a closed configuration respectively. The first 12 and second 14 portions of the apparatus 10 are rotatable relative to one another. FIG. 3 shows the apparatus 10 in the open position and FIG. 4 shows the apparatus 10 in the closed position.

The first 12 and second 14 portions of the container are semicircular in shape. The diameter of the second portion 14 is smaller than that of the first portion 12. The gap 38 in the second portion 14 is such that the pipe 18 can pass through the gap 38 into the chamber 20. The second portion 14 is then moveable relative to the first portion 12 to enclose a portion of the pipe 18, as shown in FIG. 4.

The detector 30 is attached to the second portion 14 of the container and moves with the second portion 14. When the second portion 14 is moved such that the container is in the closed position, as shown in FIG. 4, the detector is located under the pipe, opposite to the source of radiation 16. The beam of radiation 28 is therefore able to pass through a cross-section of the pipe 18 and contact the detector 30. The beam of radiation 28 is emitted by the source of radiation 16 in the second container 22 or x-ray generator (not shown), passing through apertures 24, 26 and into the chamber 20 of the container.

Figure 5:
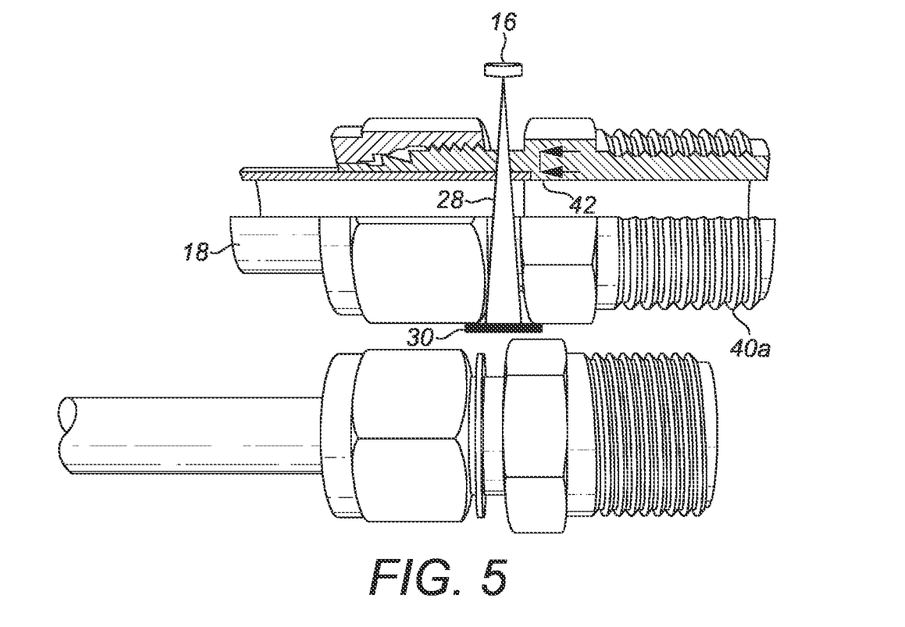
FIGS. 5 and 6 show a beam of radiation passing through a pipe and pipe fitting.
Figure 6:
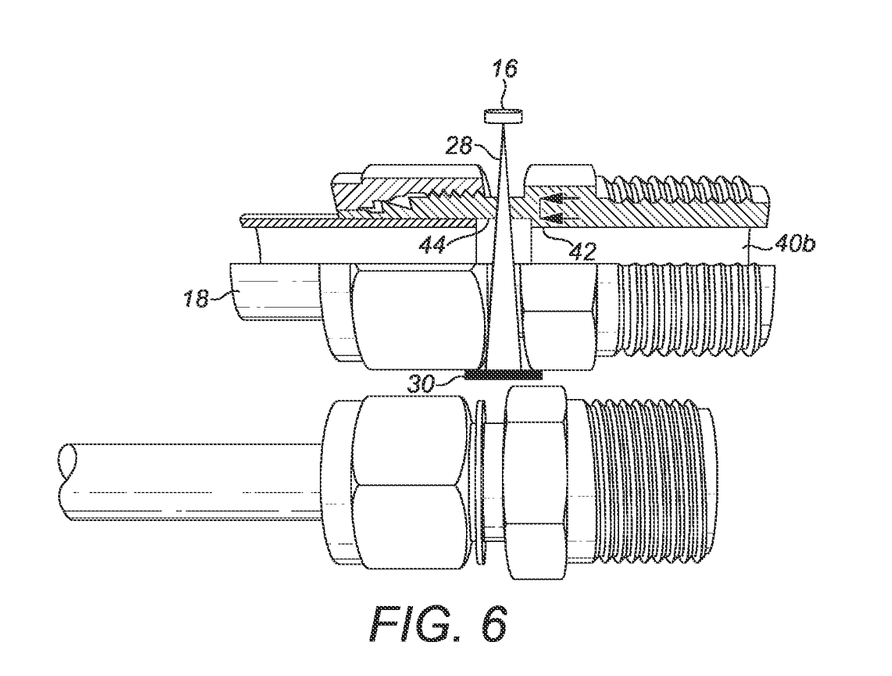

FIGS. 5 and 6 show a beam of radiation 28 passing through a pipe 18 and pipe fitting 40a and through a pipe fitting 40b respectively.

FIG. 5 shows a pipe fitting 40a where an end or an end face of the pipe 18 abuts an internal mating surface 42 of the pipe fitting 40a. FIG. 6 shows a pipe fitting 40b where the end or the end face the pipe 18 is spaced apart from the internal mating surface 42 of the pipe fitting to leave a gap 44.

The amount or strength of radiation, shown as the beam of radiation 28, passing through the pipe 18 and pipe fitting 40a, as shown in FIG. 5 is less than the amount or strength of radiation, shown by the beam of radiation 28, passing through only the pipe fitting 40b, as shown in FIG. 6. This difference can be used to determine if the pipe 18 and pipe fitting 40a, 40b have been correctly connected together, as shown in FIG. 5, or incorrectly connected together, as shown in FIG. 6. The radiation emitted by the source of radiation 16, passing through the pipe 18 and pipe fitting 40a or just the pipe fitting 40b is detected by the detector 30.

Figure 7:
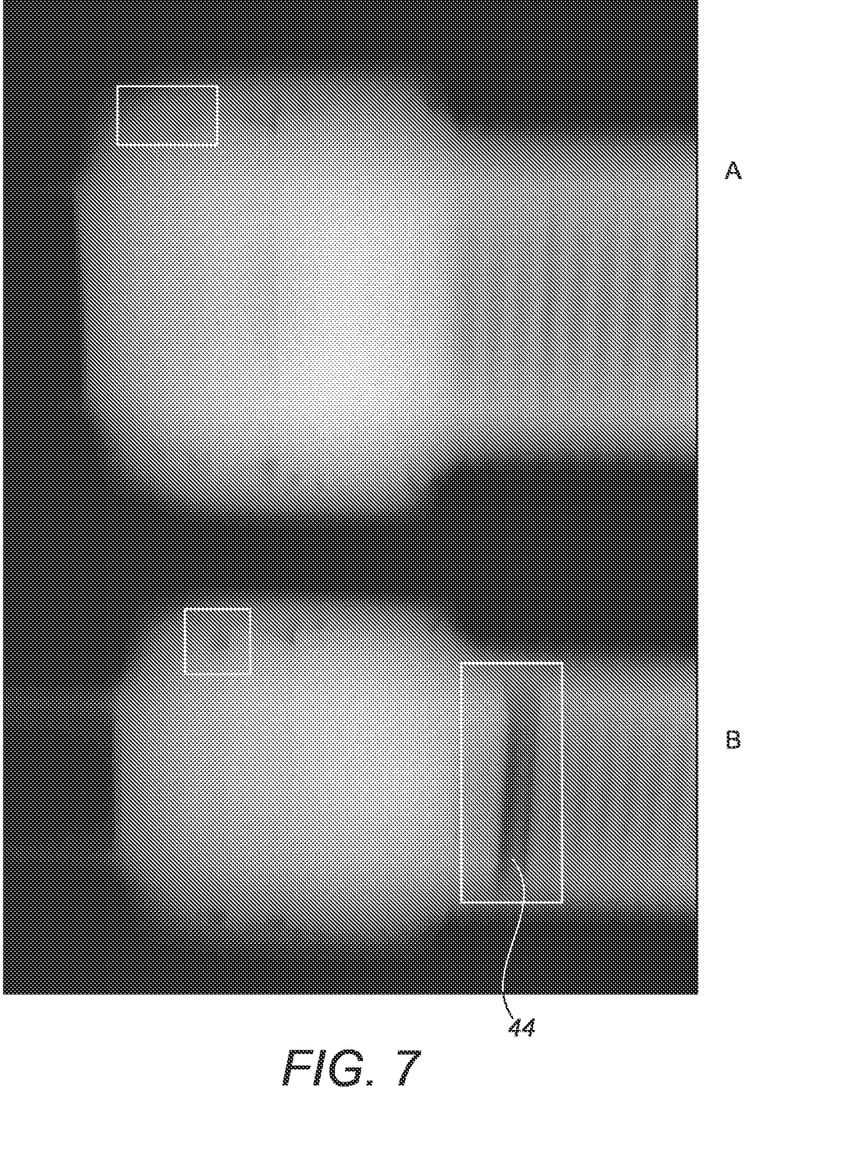
FIGS. 7A and 7B show radiographic images of a pipe and pipe fitting fitted together correctly (A) and incorrectly (B).

FIGS. 7A and 7B show radiographic images of a pipe and pipe fitting fitted together correctly (A) and incorrectly (B).

FIG. 7A is a radiograph of the pipe 18 and a typical pipe fitting 40a shown in FIG. 5. FIG. 7B is a radiograph of the pipe 18 and a typical pipe fitting 40b shown in FIG. 6. FIG. 7B shows a typical gap 44, also shown in FIG. 6.

The boxed section in FIG. 7A shows a miss-fitted back ferrule and FIG. 7B shows a correctly fitted back ferrule, The method of inspecting a pipe involves locating the first portion 12 and second portion 14 of the first container around a pipe 18 when the first container is in an open position. The first container 12, 14 is then moved from the open position to a closed position, wherein in the closed position the container 12, 14 is located around the pipe 18 and at least substantially encloses at least a portion of the pipe 18. In use, the pipe 18 typically passes through the centre of the container 12, 14. Once the container 12, 14 is in the closed position as shown in FIGS. 1, 2 and 4, radiation is emitted from the source 16 of radiation enclosed in the second container 22 or from the x-ray generator (not shown).

In use, the source of radiation 16 emits a beam of radiation 28. The radiation is ionising radiation with a wavelength of equal to or less than 100 nanometers and a frequency of equal to or more than $3 \times 10^{15}$ hertz.

The step of emitting radiation includes emitting the radiation through the container 12, 14 and/or through the at least a portion of the pipe 18 and a pipe fitting (not shown) via apertures 24, 26 which provide communication between the container 12, 14 and the second container 22 or x-ray generator (not shown). The radiation is subsequently detected by the radiation detector 30 in the second portion 14 of the container.

In use, the method includes the step of comparing the strength of the radiation able to pass through the pipe 18 and/or pipe fitting with the strength of the radiation able to pass through the container 12, 14 and/or the strength of the radiation able to pass through only the pipe fitting.

When there is a gap 44 between the pipe 18 and the pipe fitting 40b as shown in FIG. 6, the amount of radiation detected by the detector 30 is more than the amount of radiation detected by the detector 30 when the pipe 18 and the pipe fitting 40b are correctly connected or joined together, as shown in FIG. 5.

The amount of radiation able to pass through a section or portion of pipe 18 where the thickness of the wall of the pipe has been reduced, by for example corrosion, is more than the amount of radiation able to pass through an un-corroded portion of the same pipe 18. Blockages in the pipe 18 or pipe fitting 40a will cause less radiation to pass through to the detector 30 in comparison to an unblocked pipe or fitting Modifications and improvements can be incorporated herein without departing from the scope of the invention.

The invention claimed is:

1. A method of inspecting a pipe, the method including the steps of:
    providing a container comprising a first portion and a second portion that form a chamber in a closed position;
    locating the container around a pipe when the container is in an open position;
    moving the container from the open position to the closed position, wherein in the closed position the container is located around the pipe and substantially encloses at least a portion of the pipe within the chamber; and
    passing a beam of radiation across the chamber of the container and through the at least a portion of the pipe when the container is in the closed position, wherein the container shields the beam of radiation, wherein a center of the beam of radiation is perpendicular to a longitudinal axis along a length of the pipe, a distance between a source of the radiation and the at least a portion of the pipe being equal to or less than 300 mm, wherein the container comprises a radiation detector attached to and movable with the second portion of the container, the radiation detector configured to determine a strength, quantity, and/or amount of radiation, wherein the radiation detector is located in the container opposite to the source of radiation when in the closed position.

2. A method according to claim 1, wherein the at least a portion of the pipe includes a pipe fitting.

3. A method according to claim 1, wherein the distance between the source of radiation and the at least a portion of the pipe is equal to or less than 100 mm.

4. A method according to claim 1, wherein the container further comprises a safety system to at least mitigate an emission of radiation from the source of radiation into the container, when the container is in the open position.

5. A method according to claim 1, wherein the source of radiation has a wavelength of equal to or less than 100 nanometers.

6. A method according to claim 1, wherein the source of radiation has a frequency of equal to or more than $3\times10^{15}$ Hz.

7. A method according to claim 1, wherein the container totally shields the beam of radiation.

8. A method according to claim 2, wherein the method includes the step of comparing the strength of the radiation able to pass through the pipe and pipe fitting with the strength of the radiation able to pass across the container.

9. A method according to claim 4, wherein the safety system is a shield, the shield comprising the second portion of the container.

10. An apparatus comprising:
a container comprising a first portion and a second portion, the container being moveable between an open and a closed position, wherein in the open position the container is locatable around a pipe and in the closed position the first portion and the second portion of the container form a chamber that substantially encloses at least a portion of the pipe within the chamber;
a source of radiation enclosed in the container and positioned to pass a beam of radiation across the chamber of the container in the closed position, wherein the container shields the beam of radiation, wherein a center of the beam of radiation is perpendicular to a longitudinal axis along a length of the pipe;
wherein in the closed position a distance between the source of radiation and the at least a portion of the pipe is equal to or less than 300 mm; and
a radiation detector attached to and movable with the second portion of the container, the radiation detector configured to determine a strength, quantity, and/or amount of radiation, wherein the radiation detector is located in the container opposite to the source of radiation when in the closed position.

11. An apparatus according to claim 10, wherein the pipe has a pipe fitting at one end.

12. An apparatus according to claim 10, wherein the distance between the source of radiation and the at least a portion of the pipe is equal to or less than 100 mm.

13. An apparatus according to claim 10, wherein the apparatus further comprises a safety system to at least mitigate an emission of radiation from the source of radiation into the container, when the container is in the open position.

14. An apparatus according to claim 10, wherein the source of radiation has a wavelength of equal to or less than 100 nanometers.

15. An apparatus according to claim 10, wherein the source of radiation has a frequency of equal to or more than $3\times10^{15}$ Hz.

16. An apparatus according to claim 10, wherein the container comprises a first container and a second container, the first container comprising the first portion and the second portion, the second container attachable to the first container, wherein the second container comprises the source of radiation.

17. An apparatus according to claim 11, wherein in the closed position the container substantially encloses the at least a portion of the pipe and the pipe fitting.

18. An apparatus according to claim 13, wherein the safety system is a shield, the shield comprising the second portion of the container.

19. An apparatus according to claim 16, wherein the first container has an aperture for communication with an aperture in the second container, and wherein the apertures are aligned in the closed position such that the source of radiation in the second container provides the source of radiation in the first container.

20. An apparatus comprising:
a container comprising a first portion and a second portion, the container being moveable between an open and a closed position, wherein in the open position the container is locatable around a pipe and in the closed position the first portion and the second portion of the container form a chamber that substantially encloses at least a portion of the pipe within the chamber;
a source of radiation enclosed in the container and positioned to pass a beam of radiation across the chamber of the container in the closed position, wherein the container shields the beam of radiation; and
a radiation detector attached to and movable with the second portion of the container, the radiation detector configured to determine a strength, quantity, and/or amount of radiation, wherein the radiation detector is located in the container opposite to the source of radiation when in the closed position.

21. An apparatus according to claim 20, wherein the container comprises a first container and a second container, the first container comprising the first portion and the second portion, the second container attachable to the first container, wherein the second container comprises the source of radiation.

22. An apparatus according to claim 20, wherein in the closed position a distance between the source of radiation and the at least a portion of the pipe is equal to or less than 300 mm.

23. An apparatus according to claim 21, wherein the first container has an aperture for communication with an aperture in the second container, and wherein the apertures are aligned in the closed position such that the source of radiation in the second container provides the source of radiation in the first container.

* * * * *